(12) United States Patent
Im et al.

(10) Patent No.: US 7,070,610 B2
(45) Date of Patent: Jul. 4, 2006

(54) MONOFILAMENT SUTURE AND MANUFACTURING METHOD THEREOF

(75) Inventors: Jung-nam Im, Dae-jeon (KR); Jang-il Seo, Dae-jeon (KR); Chong-taek Hong, Dae-jeon (KR); Hye-sung Yoon, Dae-jeon (KR); Chaul-min Pai, Dae-jeon (KR)

(73) Assignee: Samyang Corporation (KR)

( * ) Notice: Subject to any disclaimer, the term of this patent is extended or adjusted under 35 U.S.C. 154(b) by 321 days.

(21) Appl. No.: 10/218,336

(22) Filed: Aug. 13, 2002

(65) Prior Publication Data

US 2003/0187476 A1    Oct. 2, 2003

(30) Foreign Application Priority Data

Mar. 30, 2002    (KR)    ............... 2002-17609

(51) Int. Cl.
    *A61L 17/00*    (2006.01)
(52) U.S. Cl. ................................... 606/230
(58) Field of Classification Search ........ 606/228–231; 132/321
    See application file for complete search history.

(56) References Cited

U.S. PATENT DOCUMENTS

| | | | |
|---|---|---|---|
| 4,470,941 A | 9/1984 | Kurtz | |
| 4,620,542 A | 11/1986 | Menezes et al. | |
| 5,225,520 A * | 7/1993 | Kennedy et al. | 528/354 |
| 5,451,461 A | 9/1995 | Broyer | |
| 5,456,696 A | 10/1995 | Liu | |
| 5,578,046 A | 11/1996 | Liu et al. | |
| 5,626,611 A | 5/1997 | Liu et al. | |
| 5,641,501 A | 6/1997 | Cooper et al. | |
| 5,674,286 A * | 10/1997 | D'Alessio et al. | 424/423 |
| 5,997,568 A | 12/1999 | Liu | |
| 6,090,910 A | 7/2000 | Shinoda et al. | |
| 6,093,200 A | 7/2000 | Liu et al. | |
| 6,162,537 A | 12/2000 | Martin et al. | |
| 6,183,499 B1 | 2/2001 | Fischer et al. | |
| 6,191,236 B1 | 2/2001 | Roby et al. | |
| 6,197,043 B1 | 3/2001 | Davidson | |
| 6,235,869 B1 | 5/2001 | Roby et al. | |

(Continued)

FOREIGN PATENT DOCUMENTS

| | | |
|---|---|---|
| EP | 0 499 204 A1 | 8/1992 |
| EP | 0 668 083 A1 | 8/1995 |
| EP | 0 786 259 A2 | 7/1997 |

(Continued)

OTHER PUBLICATIONS

Rao S.Bezwada et al; Monocryl® Suture, A New Ultra-Pliable Absorbable Monofilament Suture, *Biomaterials* 1995, 16:1141-1148.

(Continued)

*Primary Examiner*—Eduardo C. Robert
*Assistant Examiner*—D. Jacob Davis
(74) *Attorney, Agent, or Firm*—Thorpe North & Western, LLP (57) ABSTRACT

The present invention relates to a monofilament suture prepared by co-extruding polymers having different Young's moduli and to a process for preparing the same. The suture is prepared in such a form that a polymer having a high Young's modulus surrounds a polymer having a low Young's modulus. The monofilament suture prepared by the present invention has excellent knot security, flexibility and/or knot strength.

10 Claims, 6 Drawing Sheets

U.S. PATENT DOCUMENTS

| | | |
|---|---|---|
| 6,315,788 B1 | 11/2001 | Roby |
| 6,342,065 B1 | 1/2002 | Shalaby |
| 2004/0010286 A1* | 1/2004 | Gieringer .................. 606/228 |

FOREIGN PATENT DOCUMENTS

| | | |
|---|---|---|
| EP | 1 216 718 A1 | 6/2002 |
| GB | WO 00/01426 | 1/2000 |
| KR | 99010319 | 2/1999 |
| US | WO 98/20190 | 5/1998 |
| US | WO 99/34750 | 7/1999 |
| US | WO 00/22991 | 4/2000 |

OTHER PUBLICATIONS

E.J.C. Van Rijssel et al; Tissue Reaction and Surgical Knots: The Effect of Suture Size, Knot Configuration, and Knot Volume, *Obstet Gynecol* 1989; 74:64-8.

J. B. Trimbos; Security of Various Knots Commonly Used in Surgical Practice, *Obstet Gynecol 1984*, 64:274-80.

E.J.C. Van Rijssel et al; Mechanical Performance of Square Knots and Sliding Knots in Surgery: A Comparative Study, *Am J Obstet Gynecol* 1990; 162:93-7.

* cited by examiner

MONOFILAMENT SUTURE AND MANUFACTURING METHOD THEREOF

This application claims benefit of Korean Patent Application No. 2002-17609 filed on Mar. 30, 2002.

FIELD OF THE INVENTION

This invention relates to a monofilament suture having excellent knot security and flexibility, and to a process for the manufacture of the same.

BACKGROUND OF THE INVENTION

Monofilament sutures generally exhibit less tissue drag and causes less tear because they have smoother surfaces than braided multifilament sutures. Monofilament sutures, in general, do not provide the capillarity found in multifilament sutures, which would minimize the spread of wound infection with bacteria and the like. However, since monofilament sutures comprise a single filament there are the following disadvantages: they are less flexible than multifilament sutures; it is more difficult to tie a knot; and the tied knot is more likely to loosen due to inferior knot security.

Particularly, monofilament sutures are less flexible, which results in difficulties in handling and in tying during surgical operations. Moreover, due to the fact that the ears of the tied suture remaining inside the body may irritate adjacent tissues, patients often complain of pain. In addition, even if a marketed monofilament suture is relatively flexible, its knot is easily untied. Therefore, in order to make the knot secure additional throws while tying are required. Such additional throws increase the amount of suture remaining inside the body, and, consequently, increase the irritation caused by the foreign material in the wound. The increase in foreign body, even in the case of an absorbable suture with good biocompatibility, may provoke irritation in adjacent tissue, and thus, increase the probability of inflammation. Furthermore, a patient may feel sensations or stimulation from the knots. The larger the volume of tied knots there is, the more likely it is that undesirable symptoms will present. Van Rijssel E J C, et al., Mechanical performance of square knots and sliding knots in surgery: A comparative study, *Am J Obstet Gynecol* 1990; 162:93–7, Van Rijssel E J C, et al.; Tissue reaction and surgical knots: the effect of suture size, knot configuration, and knot volume, *Obstet Gynecol* 1989; 74:64–8; and Trimbos, J. B., Security of various knots commonly used in surgical practice, *Obstet Gynecol.*, 64:274–80, 1984.

In order to overcome on the above disadvantages of a monofilament suture, various methods for improving flexibility of monofilaments have been developed. For example, there is disclosed a process for manufacturing monofilament sutures by modification of a homopolymer (U.S. Pat. No. 5,451,461) or by using a copolymer (Monocryl® suture, a new ultra-pliable absorbable monofilament suture, *Biomaterials*, v16, 1995, pp 1141–1148). However, the process has limits in improving the flexibility of the suture. Also, even when flexibility is improved, the problem of poor knot security remains. When two or more polymers are combined together, disadvantages of one polymer may be offset by advantages of the others.

U.S. Pat. Nos. 5,626,611; 5,641,501; 6,090,910; and 6,162,537 disclose processes for preparing a suture by using different polymers. However, they are for techniques for controlling the absorption rate when absorbable sutures are degraded in the body. U.S. Pat. Nos. 5,641,501 and 6,090,910 relate to sutures prepared by physically mixing two kinds of polymers. When two polymers are physically mixed and spun into a yarn, the two polymers are not homogeneously distributed over each other, and phases of melted polymers are easily separated therewith. Thus, it is hard to spin the polymers into yarn and it is difficult to make the sutures have homogeneous physical properties.

U.S. Pat. No. 5,626,611 relates to a suture prepared by co-extruding polymers into a sheath/core type, in order to control the absorption rate of the suture. That is, it relates to a method for controlling the absorption rate in accordance with the absorption rate of each polymer used in the sheath or core portion. U.S. Pat. No. 6,162,537 relates to a process for co-extruding a non-absorbable polymer and an absorbable polymer, in order to improve the biologic response of non-absorbable polymers in the body.

As described above, there has been much research in improving the flexibility and strength of sutures and into the techniques for controlling absorption rates. However, research into improving knot security, as one of the important requirements of a suture, has not been enough. Therefore, the present invention provides a suture with excellent knot security and flexibility, which helps overcome the disadvantages of currently marketed monofilament sutures.

SUMMARY OF THE INVENTION

The present invention provides a monofilament suture that exhibits excellent knot security, flexibility and/or knot strength.

The present invention also provides a process for manufacturing a suture by a co-extrusion method that can improve spinnability.

The present invention relates to a monofilament suture prepared by co-extruding polymers with different Young's moduli and to a process for preparing the same. The suture of the present invention has excellent knot security and flexibility. The term "Young's modulus" in the present invention means a value obtained by measuring the tensile strength of yarns prepared by spinning the polymers under suitable conditions and drawing them at a draw ratio of 3~12.

The monofilament suture of the present invention is prepared by co-extruding the polymer having a high Young's modulus (first polymer) and the other polymer having a low Young's modulus (second polymer) into a form so that the first polymer surrounds the second polymer. One type of suture suitable for the present invention is a sea/island type wherein the first polymer, having a high Young's modulus, is a sea component and the second polymer, having a low Young's modulus, is an island component. Another suitable type of suture of the present invention is a sheath/core type prepared from the first polymer, having a high Young's modulus, as a sheath component and the second polymer having a low Young's modulus, as a core component.

The kinds of polymers used in the present invention are not limited, as long as they have a form so that the first polymer, with a high Young's modulus, surrounds the second polymer, with a low Young's modulus. The first polymer, or the second polymer, may be a homopolymer or a copolymer and preferably is a bioabsorbable polymer. Preferably, the first or the second polymer is a homopolymer prepared from the group consisting of glycolide, glycolic acid, lactide, lactic acid, caprolactone, dioxanone, trimethylene carbonate, ethylene glycol, derivatives thereof and copolymers thereof. For example, polycaprolactone and a copolymer thereof, a copolymer of polylactide, a copolymer of polyglycolic acid, a copolymer of trimethylene carbonate and the like may be used as the second polymer. Preferably, the first polymer is polyglycolic acid, polydioxanone, polylactide or a copolymer thereof, and the second polymer is polycaprolactone, trimethylene carbonate, a homopolymer of DL-polylactide or a copolymer thereof.

In the present invention, a given polymer may be used as the first polymer or the second polymer. That is, even though the same polymer is used, the position of the polymer depends on the Young's modulus of the other polymer used when co-extruding them. Specifically, when a sea/island type suture is prepared by using polydioxanone and polycaprolactone, polydioxanone is used as the sea component (the first polymer) and polycaprolactone as the island component (the second polymer), since the Young's modulus of polydioxanone is higher than that of polycaprolactone. However, when polydioxanone and polyglycolic acid are co-extruded into a sea/island type, polydioxanone must be used as the island component (the second polymer) and polyglycolic acid as the sea component (the first polymer), since the Young's modulus of polydioxanone is lower than that of polyglycolic acid.

In the present invention, co-extrusion of the polymers into the sea/island type is more desirable than co-extrusion of the polymers into the sheath/core type. Even though the content ratios of the two polymers used are the same, the cross-sectional shape of the suture prepared by the sea/island type is greatly deformed by tying the knot, and thus, surface friction force is increased even more. Therefore, the suture made by co-extrusion of the polymers into the sea/island type of the present invention gives excellent knot security.

Generally, fibers become more flexible when their stiffness is low. Stiffness varies with cross sectional shape of the fibers, even when they have the same cross-sectional area. The sea/island type suture is more flexible than the sheath/core type suture, due to the cross-sectional shape of the second polymer. It is generally believed that stiffness of the sea/island type suture is low. However, among sea/island type sutures with the same component ratios, the physical properties of the suture may vary depending on the number of islands or the arrangement of the islands.

Figure 4A:
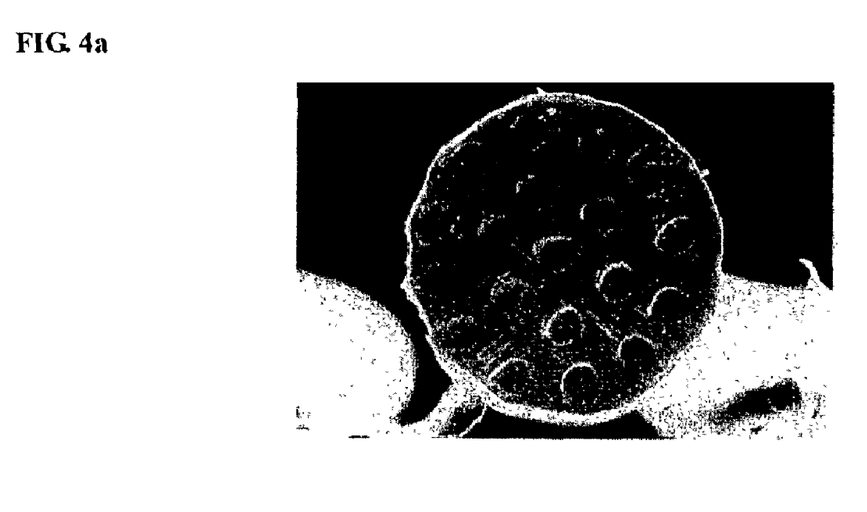
FIG. 4a is an SEM photograph showing a cross-section of the suture obtained by co-extruding a polymer with a high Young's modulus surrounding a polymer with a low Young's modulus.
Figure 4B:
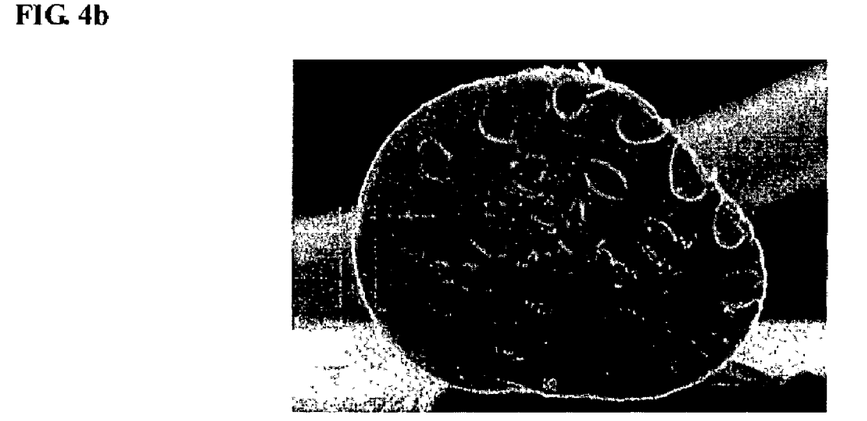
FIG. 4b is an SEM photograph showing a cross-section of the suture obtained by co-extruding a polymer with a low Young's modulus surrounding a polymer with a high Young's modulus.

Preferably, in the present invention, the first polymer, having a higher Young's modulus, also has a higher melting point than the second polymer. When co-extruding the first polymer, whose Young's modulus and melting point are lower than the second polymer, the resulting suture is not round in cross-section (Ref. FIG. 4b), and has poor knot strength. Therefore, it is not suitable for use as a suture. If the cross-sectional roundness of a suture deteriorates, the suture is apt to cause tissue dragging and difficulties in needle attachment, and therefore, it is not suitable for use as a suturing material.

In the present invention, the amount of the first polymer is preferably 10–90% by volume, and the amount of the second polymer is preferably 10–90% by volume. When the amount of each polymer is less than 10% by volume, a cross section of the obtained suture does not clearly distinguish between the first polymer and the second polymer. Thus, it is preferred that each polymer is used in an amount of 10% by volume or more. More preferably, the amount of the first polymer is 50–90% by volume and the amount of the second polymer is 10–50% by volume. When the amount of the second polymer is 50% or more, the surface layer of first polymer becomes too thin. Therefore, there is an operational problem in that the second polymer is drawn near the surface of the suture and the resulting yarn is likely to break during the manufacturing process. In addition, when an annealing process is carried out, for improving the mechanical properties of the suture, the second polymer, the amount of which is too large, is likely to be exposed outward from the first polymer, and thus, the surface of the suture is apt to be rough. When the surface becomes rough, the suture will likely causes damage such as tissue dragging.

Preferably, the first polymer and the second polymer used in the present invention are polymers that have a Young's modulus of 3.0 GPa or less. When the Young's modulus is more than 3.0 GPa, the obtained suture is not suitable for use as a monofilament suture, since its flexibility is lowered, even though the polymers are co-extruded. More preferably, the first polymer has a Young's modulus of 2.0 GPa or less. If the Young's modulus of the first polymer is high, it will easily cause shape deformation of the monofilament and cause surface unevenness and/or cracking of the knot, when it is tied, which in turn provides the advantage of improving knot security. However, when the Young's modulus of the first polymer is too high, i.e. 2.0 GPa or more, flexibility of the monofilament is lowered even when the monofilaments are prepared by co-extruding.

In the present invention, the second polymer preferably has a Young's modulus of 1.5 GPa or less, and more preferably, the second polymer has a Young's modulus of 1.2 GPa or less. The sutures become more flexible when the Young's moduli of the polymers are lower.

More preferably, a polymer having Young's modulus of 1.0~1.5 GPa is used as the first polymer with the second polymer having a Young's modulus of at least 0.3 GPa lower than the Young's modulus of the first polymer.

The surface unevenness, by knot tying, is larger when the difference of the Young's moduli between the first polymer and the second polymer is larger. Therefore, it is preferred that the second polymer of the present invention has a Young's modulus of 0.4~1.2 GPa.

The suture obtained by the present invention has excellent knot security and flexibility. Therefore, it may be used in soft tissue patches, surgical mesh, thin film type dressings, surgical felts, artificial blood vessels, auxiliary materials for treating nerves, artificial skins, sternum tapes, sutures and the like.

In addition to promoting wound repair and/or tissue growth a small amount of a drug may be added to the first polymer or the second polymer. Also, for improving knot security and flexibility, a small amount of various polymers and/or additives may be added to one of the above polymers. Therefore, the purpose of the present invention also includes co-extruding these polymers with the first and the second polymer of the present invention.

DETAILED DESCRIPTION THE INVENTION

This invention is not limited to the particular configurations, process steps, and materials disclosed herein, as such configurations, process steps, and materials may vary somewhat. It is also to be understood that the terminology employed herein is used for the purpose of describing particular embodiments only, and is not intended to be limiting since the scope of the present invention will be limited only by the appended claims and equivalents thereof.

In this specification and the appended claims, the singular forms "a," "an," and "the" include plural references unless the context clearly dictates otherwise. In describing and claiming the present invention, the following terminology will be used in accordance with the definitions set out below.

"Biodegradable polymer" and "absorbable polymer" means that the polymer can chemically break down or degrade within the body to form nontoxic components.

Figure 1A:
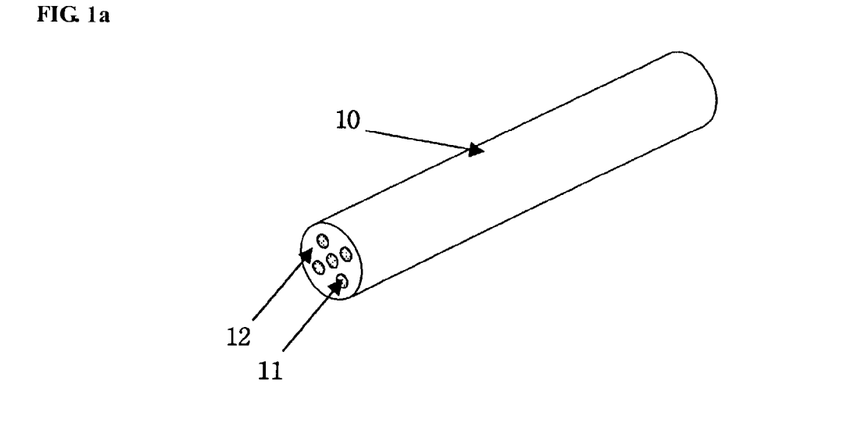
FIGS. 1a and 1b are schematic prespective views of the final filament shape to be realized by the present invention (1a: sea/island type, 1b: sheath/core type).
Figure 1B:
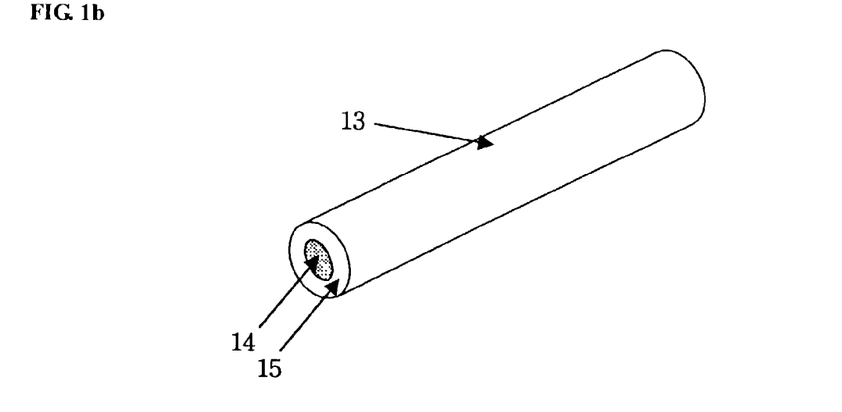

The present invention relates to preparing monofilament sutures by co-extrusion of two biodegradable polymers having different Young's Moduli, which is explained in view of the attached figures as follows:

FIGS. 1a and 1b illustrate the final shapes of the filaments to be embodied by the present invention. A monofilament 10 is co-extruded in the sea/island type, wherein the island component 11 is surrounded by the sea component 12. A monofilament 13 is co-extruded in the sheath/core type, wherein the core component 14 is surrounded by the sheath component 15. Since the components making up the filaments and their sutures affect the physical properties, the characteristics of each filament 10, 13 are different from those of conventional coated filaments.

Figure 2:
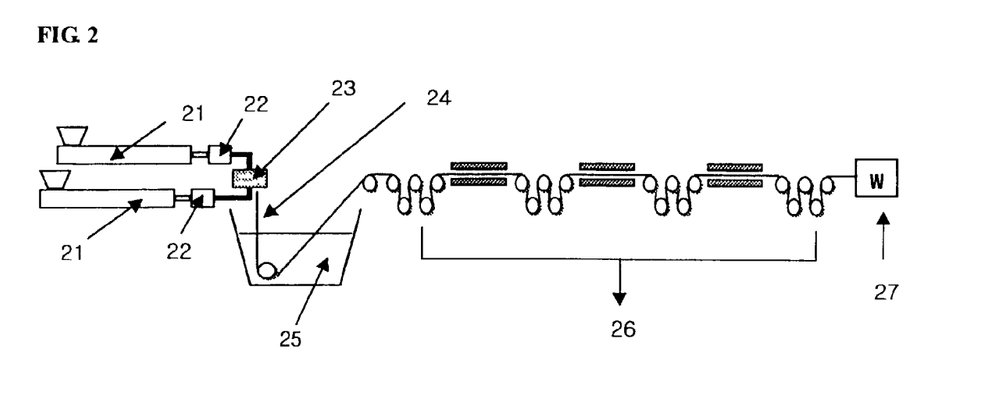
FIG. 2 illustrates schematically a process for manufacturing the suture to be obtained in the present invention.

FIG. 2 schematically illustrates the conventional manufacturing process used to produce co-extruded monofilaments having the structure of the present invention. Specifically, in the co-extrusion process, each polymer is separately melted by two extruders 21. The melted polymers flow out in the desired amounts through the metering pumps 22. By controlling the amounts that flow, the content ratio of each polymer can be controlled in the co-extruded polymers.

The melted polymers, which flowed out through metering pump 22, are combined in the manner, shown in FIG. 3, into filament 24 through spin block 23. Although a single filament is shown for simplification in FIG. 2, it is understood that spinnerets having any desired number of exiting orifices may be used. The melted filament 24 is solidified in quenching bath 25. The air gap is the distance between the spinneret exit and the bath. Preferably the air gap distance ranges from 0.5 to 100 centimeters and, more preferably, from about 1 to 30 centimeters. The solidified yarn 24 is drawn with drawing system 26 in order to achieve the desired orientation and improve the physical properties. After that, the finished monofilament product is wound to winder 27. Alternatively, in order to improve the physical properties of the suture, the solidified yarn 24 is not directly drawn, but is wound in the form of undrawn yarn (UDY). It may be aged under appropriate conditions, and then, drawn by a drawing system to prepare the drawn yarn. Following the drawing process, the monofilament 24 may be annealed to further improve its properties.

Figure 3A:
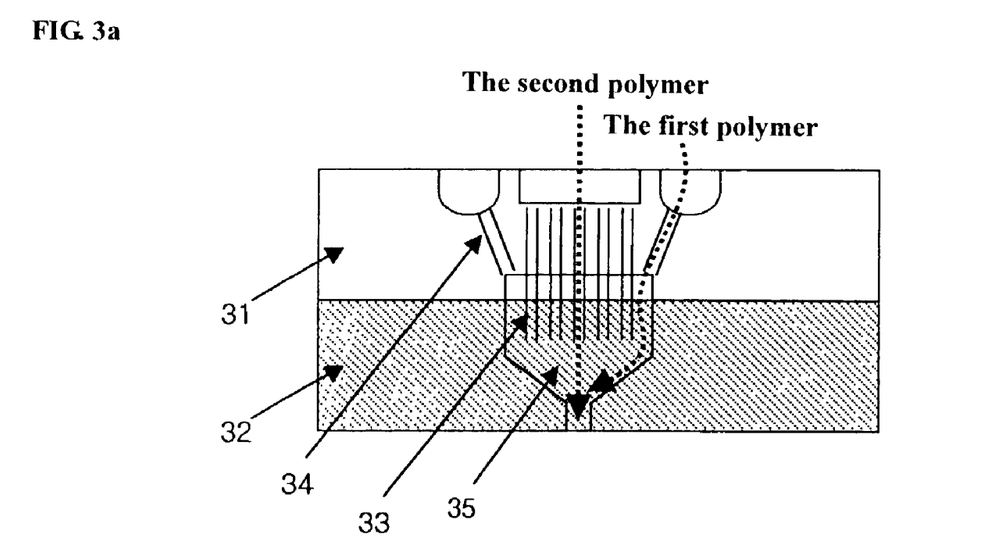
FIGS. 3a and 3b illustrate schematically a spinning pack (nozzle pack) (3a: the spinning pack for preparing the sea/island type, 3b: the spinning pack for preparing the sheath/core type).
Figure 3B:
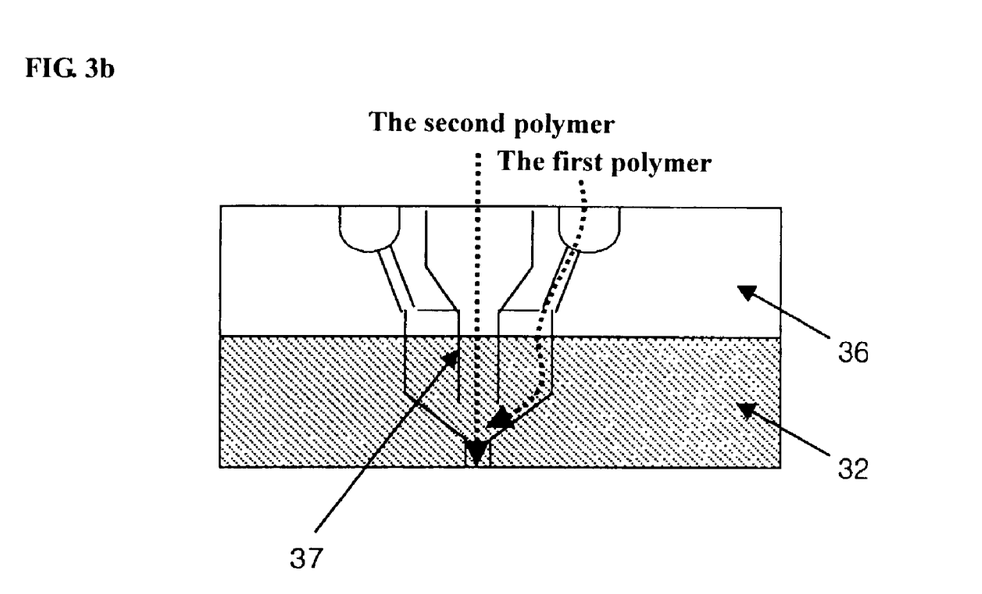

FIGS. 3a and 3b illustrate examples of a spin pack which may be used as a spin block 23 in the present invention and which comprises a nozzle and distribution plates and the like. The first polymer and the second polymer are melted through each extruder, passed through distribution plates 31 and 36, and each flow into a nozzle 32, where the melted polymers are joined thus forming a continuous polymer melt.

Specifically, FIG. 3a is an example of the spin pack for obtaining a sea/island type suture. The first polymer and the second polymer pass through distribution plates 31. The second polymer, passing through flow channels 33, becomes the island component, and the first polymer, passing through flow channels 34, becomes the sea component surrounding the second polymer.

The number of flow channels 33 varies with the desired physical properties of the final filament. If the number of flow channels is one, the polymers become a co-extruded sheath/core type filament as shown in FIG. 3b. FIG. 3b is an example of the spin pack for preparing a sheath/core type suture. The melted second polymer, used to form the core component, passes through the center flow channel 37, and the melted first polymer passing through outer flow channel is incorporated into a single filament at the nozzle 32.

In the suture obtained by the above process, knot security, flexibility and strength of the suture may be controlled by using polymers having Young's moduli, strengths and melting points which are different from each other and controlling the content ratio of each polymer.

The present invention improves the knot security and flexibility of a suture by co-extruding polymers having different Young's moduli to prepare a monofilament suture in a form so that a polymer with a high Young's modulus surrounds a polymer with a low Young's modulus. The suture obtained by the present invention may be used as a medical appliance such as an artificial tendon, soft tissue patch, surgical mesh, thin film type dressing, surgical felt, artificial blood vessel, artificial skin, sternum tape and the like as well as be used as a suture.

The present invention, hereinafter, is explained in more detail, based on the following examples and comparative examples. However, these examples are provided for the purpose of illustrating the present invention only, and thus, the present invention is not intended to be limited to the examples in any way.

Methods for Measuring the Physical Properties of Sutures—Knot Security

Knot security was measured in terms of the knot slippage ratio. A surgeon's knot (2=1=1) was selected for the knot tying method. The knotted sutures were placed on a tensile strength tester and pulled apart until knot breakage occurred or the knot slipped to loosen. After ten measurements, the ratio of the number of knots slipped to the total number of the knots tied indicates the knot slippage ratio. Thus, the less the ratio, the better the knot security of the suture.

Methods for Measuring the Physical Properties of Sutures—Flexibility

Most reported flexibility data of sutures are based on Young's moduli derived from measuring linear tensile strength. However, the flexibility derived from the Young's modulus may be misleading in evaluating suture material because it represents flexibility in the tensile mode, which may be quite different from the bending stiffness that a suture actually experiences during wound closure. Therefore, in the present invention, bending stiffness was measured as a barometer of flexibility. The less the value, the more flexible the suture is.

Methods for measuring the physical properties of the suture are set forth in Table 1.

TABLE 1

Methods for measuring the physical properties of the suture

| Physical Property | Method for measuring and Apparatus |
|---|---|
| Diameter, mm | EP regulation, Diameter |
| Knot strength, kgf | EP regulation, Tensile Strength Instron Corporation |
| Stiffness, mgf/mm$^2$ | Stiffness Gurley Stiffness Tester |
| Knot slippage ratio, % | Surgeon's Knot (2 = 1 = 1) Instron Corporation |

EXAMPLE 1

In this example, polydioxanone was used as the first polymer and polycaprolactone as the second polymer. A sea/island type monofilament suture was prepared in accordance with the parameters, terms and conditions as set forth in Table 2 below. By the method for measuring the physical properties explained above, diameter, knot strength, stiffness and knot slippage ratio of the prepared suture were measured.

TABLE 2

Conditions of Processing the Sea/Island Type Co-extruded Suture

| Suture Size | EP 4 | |
|---|---|---|
| Polymer | Polycaprolactone | Polydioxanone |
| Young's modulus (GPa) | 0.7 | 1.3 |
| Melting Point (° C.) | 55~65 | 95~110 |
| Process Conditions | Extrusion Conditions | |
| Extruder | Ext. 1 (Island) | Ext. 2 (Sea) |
| Number of Island Component | 19 | — |
| Extruder screw, rpm | 7.5 | 11.4 |
| Manifold* pressure (kgf/cm$^2$) | 80 | 80 |
| Temperature of Extruder (° C.) | | |
| Zone 1 | 175 | 180 |
| Zone 2 | 178 | 183 |
| Zone 3 | 180 | 185 |
| Temperature of Manifold (° C.) | 180 | 185 |
| Temperature of Metering pump (° C.) | 180 | 185 |
| Temperature of Nozzle Pack Die (° C.) | 185 | |
| Capacity of Metering pump (cc/rev) | 1.2 | 1.2 |
| Revolution of Metering pump (rpm) | 4.0 | 9.3 |
| Temperature of Quenching bath (° C.) | 23 | |
| Winding Speed of Undrawn yarn (m/min) | 13.4 | |
| Drawing Conditions | | |
| First Roller (m/min) | 4.4 | |
| Temperature of First Drawing Oven (° C.) | 110 | |
| Second Roller (m/min) | 26.6 | |
| Temperature of Second Drawing Oven (° C.) | 115 | |
| Third Roller (m/min) | 27.3 | |
| Temperature of Third Drawing Oven (° C.) | 115 | |
| Fourth Roller (m/min) | 22.0 | |
| Total Drawing Ratio | 5.0 | |

* Manifold - Connecting site between extruder and metering pump

EXAMPLE 2

In this example, a copolymer of glycolic acid and caprolactone was used as the first polymer and polycaprolactone was used as the second polymer. A sea/island type monofilament suture was prepared in accordance with the parameters, terms and conditions as set forth in Table 3 below. Using the method for measuring the physical properties explained above, diameter, knot strength, stiffness and knot slippage ratio of the prepared suture were measured.

TABLE 3

Conditions of Processing the Sea/Island Type Co-extruded Suture

| Suture Size | EP 4 | |
|---|---|---|
| Polymer | Polycaprolactone | Copolymer* |
| Young's modulus (GPa) | 0.7 | 1.1 |
| Melting Point (° C.) | 55~65 | 210~220 |
| Process Conditions | Extrusion Conditions | |
| Extruder | Ext. 1 (Island) | Ext. 2 (Sea) |
| Number of Island Component | 19 | — |
| Extruder screw, rpm | 7.6 | 22.3 |
| Manifold* pressure (kgf/cm$^2$) | 80 | 80 |
| Temperature of Extruder (° C.) | | |
| Zone 1 | 170 | 210 |
| Zone 2 | 180 | 215 |
| Zone 3 | 190 | 220 |
| Temperature of Manifold (° C.) | 190 | 230 |
| Temperature of Metering pump (° C.) | 190 | 230 |
| Temperature of Nozzle Pack Die (° C.) | 240 | |
| Capacity of Metering pump (cc/rev) | 1.2 | 1.2 |
| Revolution of Metering pump (rpm) | 8.0 | 12.0 |
| Temperature of Quenching bath (° C.) | 5 | |
| Winding Speed of Undrawn yarn (m/min) | 18.1 | |
| Drawing Conditions | | |
| First Roller (m/min) | 4.4 | |
| Temperature of First Drawing Oven (° C.) | 90 | |
| Second Roller (m/min) | 26.0 | |
| Temperature of Second Drawing Oven (° C.) | 120 | |
| Third Roller (m/min) | 29.3 | |
| Temperature of Third Drawing Oven (° C.) | 120 | |
| Fourth Roller (m/min) | 26.4 | |
| Total Drawing Ratio | 6.0 | |

*Copolymer of glycolic acid and caprolactone

EXAMPLE 3

In this example, polydioxanone was used as the first polymer and a copolymer of lactide and caprolactone were used as the second polymer. A sea/island type monofilament suture was prepared in accordance with the parameters, term and conditions as set forth in Table 4 below. Using the method for measuring the physical properties explained above, diameter, knot strength, stiffness and knot slippage ratio of the prepared suture were measured.

TABLE 4

Conditions of Processing the Sea/Island Type Co-extruded Suture

| | | |
|---|---|---|
| Suture Size | EP 3 | |
| Polymer | Copolymer* | Polydioxanone |
| Young's modulus (GPa) | 0.6 | 1.3 |
| Melting Point (° C.) | Amorphous | 95~110 |
| Process Conditions | Extrusion Conditions | |
| Extruder | Ext. 1 (Island) | Ext. 2 (Sea) |
| Number of Island Component | 37 | — |
| Extruder screw, rpm | 7.3 | 11.5 |
| Manifold* pressure (kgf/cm²) | 80 | 80 |
| Temperature of Extruder (° C.) | | |
| Zone 1 | 140 | 180 |
| Zone 2 | 145 | 183 |
| Zone 3 | 150 | 185 |
| Temperature of Manifold (° C.) | 150 | 185 |
| Temperature of Metering pump (° C.) | 150 | 185 |
| Temperature of Nozzle Pack Die (° C.) | 185 | |
| Capacity of Metering pump (cc/rev) | 1.2 | 1.2 |
| Revolution of Metering pump (rpm) | 4.0 | 9.3 |
| Temperature of Quenching bath (° C.) | 22 | |
| Winding Speed of Undrawn yarn (m/min) | 31.1 | |
| Drawing Conditions | | |
| First Roller (m/min) | 5.3 | |
| Temperature of First Drawing Oven (° C.) | 100 | |
| Second Roller (m/min) | 26.6 | |
| Temperature of Second Drawing Oven (° C.) | 105 | |
| Third Roller (m/min) | 27.7 | |
| Temperature of Third Drawing Oven (° C.) | 105 | |
| Fourth Roller (m/min) | 25.0 | |
| Total Drawing Ratio | 4.7 | |

*Copolymer of lactide and caprolactone

EXAMPLE 4

In this example, polydioxanone was used as the first polymer and polycaprolactone as the second polymer. A sheath/core type monofilament suture was prepared in accordance with the parameters, terms and conditions as set forth in Table 5 below. Using the method for measuring the physical properties explained above, diameter, knot strength, stiffness and knot slippage ratio of the prepared suture were measured.

TABLE 5

Conditions of Processing the Sheath/Core Type Co-extruded Suture

| | | |
|---|---|---|
| Suture Size | EP 4 | |
| Polymer | Polycaprolactone | Polydioxanone |
| Young's modulus (GPa) | 0.7 | 1.3 |
| Melting Point (° C.) | 55~65 | 95~110 |
| Process Conditions | Extrusion Conditions | |
| Extruder | Ext. 1 (Core) | Ext. 2 (Sheath) |
| Extruder screw, rpm | 6.8 | 11.8 |
| Manifold* pressure (kgf/cm²) | 80 | 80 |
| Temperature of Extruder (° C.) | | |
| Zone 1 | 175 | 180 |
| Zone 2 | 178 | 183 |
| Zone 3 | 180 | 185 |
| Temperature of Manifold (° C.) | 180 | 185 |
| Temperature of Metering pump (° C.) | 180 | 185 |
| Temperature of Nozzle Pack Die (° C.) | 185 | |
| Capacity of Metering pump (cc/rev) | 1.2 | 1.2 |
| Revolution of Metering pump (rpm) | 4.0 | 9.3 |
| Temperature of Quenching bath (° C.) | 21 | |
| Winding Speed of Undrawn yarn (m/min) | 13.7 | |
| Drawing Conditions | | |
| First Roller (m/min) | 4.4 | |
| Temperature of First Drawing Oven (° C.) | 110 | |
| Second Roller (m/min) | 26.6 | |
| Temperature of Second Drawing Oven (° C.) | 115 | |
| Third Roller (m/min) | 27.3 | |
| Temperature of Third Drawing Oven (° C.) | 115 | |
| Fourth Roller (m/min) | 22.0 | |
| Total Drawing Ratio | 5.0 | |

COMPARATIVE EXAMPLE 1

In this example, polycaprolactone was used as the sea component and polydioxanone as the island component. A sea/island type monofilament suture was prepared in accordance with the parameters, terms and conditions as set forth in Table 6 below. Using the method for measuring the physical properties explained above, diameter, knot strength, stiffness and knot slippage ratio of the prepared suture were measured.

TABLE 6

Conditions of Processing the Sea/Island Type Co-extruded Suture

| | | |
|---|---|---|
| Suture Size | EP 4 | |
| Polymer | Polydioxanone | Polycaprolactone |
| Young's modulus (GPa) | 1.3 | 0.7 |
| Melting Point (° C.) | 95~110 | 55~65 |
| Process Conditions | Extrusion Conditions | |
| Extruder | Ext. 1 (Island) | Ext. 2 (Sea) |
| Number of Island Component | 19 | — |
| Extruder screw, rpm | 19.2 | 7.8 |
| Manifold* pressure (kgf/cm²) | 80 | 80 |
| Temperature of Extruder (° C.) | | |
| Zone 1 | 180 | 175 |
| Zone 2 | 183 | 178 |
| Zone 3 | 185 | 180 |
| Temperature of Manifold (° C.) | 185 | 180 |
| Temperature of Metering pump (° C.) | 185 | 180 |
| Temperature of Nozzle Pack Die (° C.) | 185 | |
| Capacity of Metering pump (cc/rev) | 1.2 | 1.2 |
| Revolution of Metering pump (rpm) | 14.0 | 6.0 |
| Temperature of Quenching bath (° C.) | 8 | |
| Winding Speed of Undrawn yarn (m/min) | 25.7 | |

TABLE 6-continued

Conditions of Processing the Sea/Island Type Co-extruded Suture

Drawing Conditions

| | |
|---|---|
| First Roller (m/min) | 6.5 |
| Temperature of First Drawing Oven (° C.) | 60 |
| Second Roller (m/min) | 26.8 |
| Temperature of Second Drawing Oven (° C.) | 70 |
| Third Roller (m/min) | 27.8 |
| Temperature of Third Drawing Oven (° C.) | 70 |
| Fourth Roller (m/min) | 25.1 |
| Total Drawing Ratio | 3.9 |

COMPARATIVE EXAMPLE 2

In this example, polycaprolactone was used as the sea component and a copolymer of glycolic acid and caprolactone as the island component. A sea/island type monofilament suture was prepared in accordance with the parameters, terms and conditions as set forth in Table 7 below. Using the method for measuring the physical properties explained above, diameter, knot strength, stiffness and knot slippage ratio of the prepared suture were measured.

TABLE 7

Conditions of Processing the Sea/Island Type Co-extruded Suture

| Suture Size | EP 4 | |
|---|---|---|
| Polymer | Copolymer* | Polycaprolactone |
| Young's modulus (GPa) | 1.1 | 0.7 |
| Melting Point (° C.) | 210~220 | 55~65 |
| Process Conditions | Extrusion Conditions | |
| Extruder | Ext. 1 (Island) | Ext. 2 (Sea) |
| Number of Island Component | 19 | — |
| Extruder screw, rpm | 19.5 | 7.8 |
| Manifold* pressure (kgf/cm$^2$) | 80 | 80 |
| Temperature of Extruder (° C.) | | |
| Zone 1 | 210 | 170 |
| Zone 2 | 215 | 180 |
| Zone 3 | 220 | 190 |
| Temperature of Manifold (° C.) | 230 | 190 |
| Temperature of Metering pump (° C.) | 230 | 190 |
| Temperature of Nozzle Pack Die (° C.) | 230 | |
| Capacity of Metering pump (cc/rev) | 1.2 | 1.2 |
| Revolution of Metering pump (rpm) | 16 | 4 |
| Temperature of Quenching bath (° C.) | 5 | |
| Winding Speed of Undrawn yarn (m/min) | 22.3 | |
| Drawing Conditions | | |
| First Roller (m/min) | 4.6 | |
| Temperature of First Drawing Oven (° C.) | 60 | |
| Second Roller (m/min) | 22.7 | |
| Temperature of Second Drawing Oven (° C.) | 70 | |
| Third Roller (m/min) | 23.2 | |
| Temperature of Third Drawing Oven (° C.) | 70 | |
| Fourth Roller (m/min) | 22.0 | |
| Total Drawing Ratio | 4.8 | |

*Copolymer of glycolic acid and caprolactone

COMPARATIVE EXAMPLE 3

In this example, a copolymer of lactide and caprolactone was used as the sea component and polydioxanone as the island component. A sea/island type monofilament suture was prepared in accordance with the parameters, terms and conditions as set forth in Table 8 below. Using the method for measuring the physical properties explained above, diameter, knot strength, stiffness and knot slippage ratio of the prepared suture were measured.

TABLE 8

Conditions of Processing the Sea/Island Type Co-extruded Suture

| Suture Size | EP 4 | |
|---|---|---|
| Polymer | Polydioxanone | Copolymer* |
| Young's modulus (GPa) | 1.3 | 0.6 |
| Melting Point (° C.) | 95~110 | Amorphous |
| Process Conditions | Extrusion Conditions | |
| Extruder | Ext. 1 (Island) | Ext. 2 (Sea) |
| Number of Island Component | 37 | — |
| Extruder screw, rpm | 11.5 | 7.6 |
| Manifold* pressure (kgf/cm$^2$) | 80 | 80 |
| Temperature of Extruder (° C.) | | |
| Zone 1 | 180 | 140 |
| Zone 2 | 183 | 145 |
| Zone 3 | 185 | 145 |
| Temperature of Manifold (° C.) | 185 | 145 |
| Temperature of Metering pump (° C.) | 185 | 150 |
| Temperature of Nozzle Pack Die (° C.) | 185 | |
| Capacity of Metering pump (cc/rev) | 1.2 | 1.2 |
| Revolution of Metering pump (rpm) | 9.3 | 4.0 |
| Temperature of Quenching bath (° C.) | 21 | |
| Winding Speed of Undrawn yarn (m/min) | 41.3 | |
| Drawing Conditions | | |
| First Roller (m/min) | 7.0 | |
| Temperature of First Drawing Oven (° C.) | 60 | |
| Second Roller (m/min) | 25.5 | |
| Temperature of Second Drawing Oven (° C.) | 65 | |
| Third Roller (m/min) | 26.3 | |
| Temperature of Third Drawing Oven (° C.) | 65 | |
| Fourth Roller (m/min) | 25.0 | |
| Total Drawing Ratio | 3.6 | |

*Copolymer of lactide and caprolactone

The physical properties of sutures prepared in accordance with the above examples are set forth in Table 9 below.

TABLE 9

Physical Properties of Sutures

| | Examples | | | | Comparative Examples | | |
|---|---|---|---|---|---|---|---|
| Measuring Items | 1 | 2 | 3 | 4 | 1 | 2 | 3 |
| Size | EP 4 | EP 4 | EP 3 | EP 4 | EP 4 | EP 4 | EP 3 |
| Diameter, mm | 0.549 | 0.532 | 0.373 | 0.545 | 0.552 | 0.535 | 0.370 |
| Knot Strength, kgf | 5.5 | 6.0 | 3.3 | 4.9 | 3.1 | 3.5 | 1.8 |
| Stiffness, mgf/mm$^2$ | 80 | 72 | 55 | 106 | 100 | 85 | 73 |
| Knot slippage ratio, % | 0 | 0 | 0 | 0 | 10 | 30 | 40 |

As shown in Table 9, the physical properties of sutures prepared by using the polymer with a high Young's modulus as the first polymer in accordance with the present invention, have excellent knot security and flexibility. In addition, monofilament sutures with excellent knot strength can also be obtained.

Specifically, since sutures obtained in Example 1 and Comparative Example 1 are co-extruded by using polydioxanone and polycaprolactone, both sutures have an EP 4 size and have diameters similar to each other. However, despite having similar diameters, the suture of Example 1, using polydioxanone with a high Young's modulus as the first polymer, has a lower stiffness than that of Comparative Example 1. Therefore, it is shown that in the case of preparing s suture in accordance with the present invention, the more flexible sutures can be obtained.

In addition, in the case of preparing monofilament sutures in accordance with the present invention, the knot slippage ratio is 0%, meaning the tied knot does not loosen. However, in the case of preparing the suture in a form so that the polymer with a low Young's modulus surrounds the polymer with a high Young's modulus, as in Comparative Examples 1, 2 and 3, its knot security is lessened. Also, in the case of preparing the suture in a form so that the polymer with a low Young's modulus surrounds the polymer with a high Young's modulus, its knot strength is significantly lowered as in Comparative Example 1. In order to increase the knot strength of the suture, in the case of increasing the draw ratio, roundness is not a suitable shape to use as a suture, as shown in FIG. 4b. The reason is considered to be as follows: when drawing force is added to the polymer with a low Young's modulus, being used as the surrounding polymer under the drawing process, the shape of the polymer is easily deformed.

EXPERIMENTAL EXAMPLE 1

In order to compare the sea/island type suture with the sheath/core type suture, the sutures were prepared by extruding polydioxanone as the first polymer and polycaprolactone as the second polymer and drawing the extrudate. At this time, in the case of the sea/island type, the number of the island component was 7. The physical properties of the sutures were measured.

TABLE 10

Comparison of the physical properties of the sea/island type suture with the sheath/core type suture

|  |  | Knot strength (GPa) | Stiffness (mgf/mm$^2$) |
|---|---|---|---|
| PDO 50% | Sea/island type | 0.134 | 57 |
| PCL 50% | Sheath/core type | 0.117 | 122 |
| PDO 70% | Sea/island type | 0.182 | 99 |
| PCL 30% | Sheath/core type | 0.131 | 99 |

As shown in Table 10, the knot strength of the suture prepared by co-extruding the polymers to form the sea/island type is better than that of the suture prepared by co-extruding the polymers to form the sheath/core type. In addition, since the sea/island type suture is less stiff its flexibility is excellent.

EXPERIMENTAL EXAMPLE 2

When a monofilament suture is prepared in a form such that the polymer having a low Young's modulus and a low melting point surrounds the polymer having a high Young's modulus and a high melting point, the roundness of the suture is likely to be less during the drawing process. FIG. 4a is a photograph showing a cross section of a suture prepared by using polydioxanone having a high Young's modulus and a high melting point as the sea component, and polycaprolactone having a low Young's modulus and a low melting point as the island component. The suture was prepared under the conditions set forth in Example 1, and shows that the roundness of a cross section of the suture is good and its shape is stable. FIG. 4b is a photograph showing a cross section of a suture prepared by using polycaprolactone as the sea component and polydioxanone as the island component as in Comparative Example 1. The results show that the resulting shape is not suitable for use as a suture since there is is significantly less roundness of the cross section. When the suture has a cross section such as that seen in FIG. 4b, attachment of the needle to the suture is difficult. In practical use, a suture having the cross section shape as in FIG. 4b, which is nearly planar, is likely to cause tissue dragging.

EXPERIMENTAL EXAMPLE 3

In order to show the beneficial effects of the present invention, the suture of the present invention was compared with sutures prepared by singly using polydioxanone and polycaprolactone, and a copolymer (Monocryl®) having improved flexibility. The results are set forth in Table 11 below.

TABLE 11

Comparison of the physical properties in accordance with the process for preparing a suture (EP 4 size)

| Sample | Component | Stiffness (mgf/mm$^2$) | Knot slippage ratio % |
|---|---|---|---|
| PDO | Polydioxanone (single extrusion) | 149 | 50 |
| PCL | Polycaprolactone (single extrusion) | 33 | 90 |
| Example 1 | Polydioxanone/Polycaprolactone (co-extrusion) | 80 | 0 |
| Monocryl ® | Copolymer of glycolide and caprolactone (single extrusion) | 105 | 60 |

As shown in Table 11, sutures made by co-extruding one polymer with polycaprolactone or copolymers thereof have significantly improved flexibility compared to those formed from the process of singly extruding polydioxanone. However, even though they have similar stiffness, the knot slippage ratio, as a barometer of knot security, varies depending on the process used for preparing the suture. When polydioxanone and polycaprolactone were co-extruded, the knot did not slip at all, showing a knot slippage ratio of 0%. However, single extrusion of a homopolymer of polydioxanone, a homopolymer of polycaprolactone, and the copolymer of glycolide and caprolactone showed a knot slippage ratio of 50% or more.

Figure 5A:
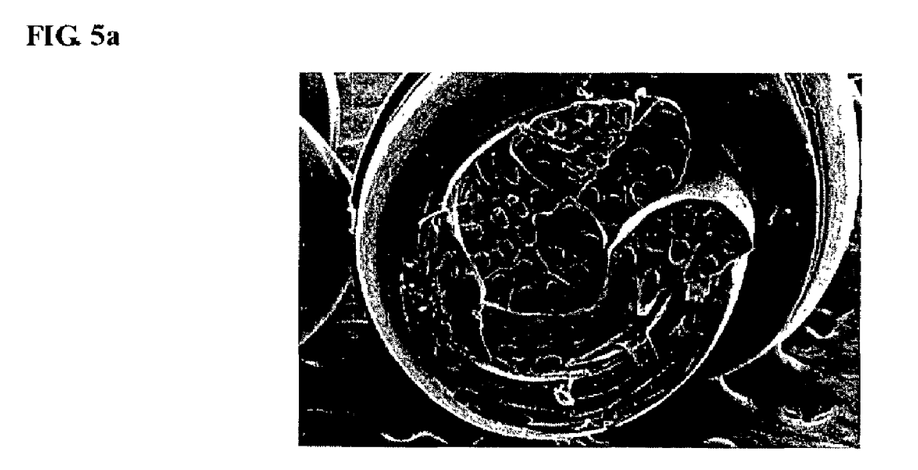
FIGS. 5a and 5b are SEM photographs showing cross-sections of knots tied with the sutures obtained by the present invention.
Figure 5B:
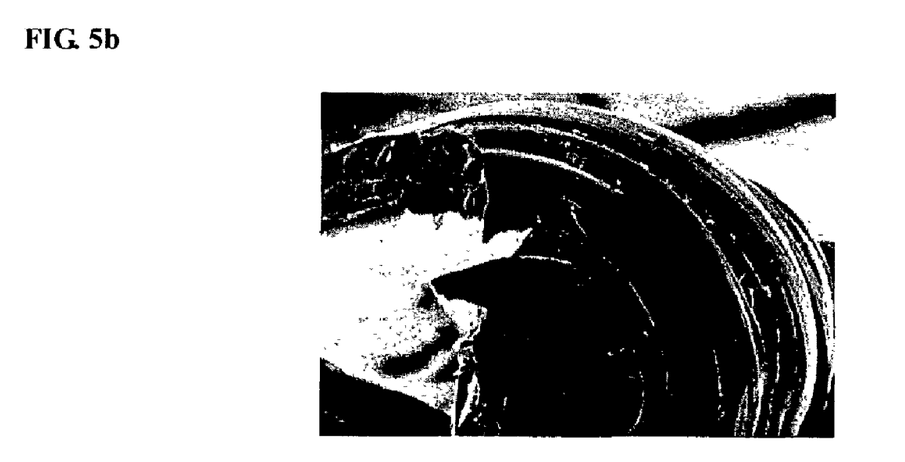

When a knot is tied, normal force is added in a direction perpendicular to the length direction of the filament. If a polymer having a high Young's modulus is used as the first polymer, in accordance with the present invention, unevenness and/or cracking occurs at the site receiving the knot tying force as shown in FIGS. 5a and 5b, and the shape of the knot is easily deformed. Therefore, knot security is improved as the friction force of the surface increases.

Figure 6A:
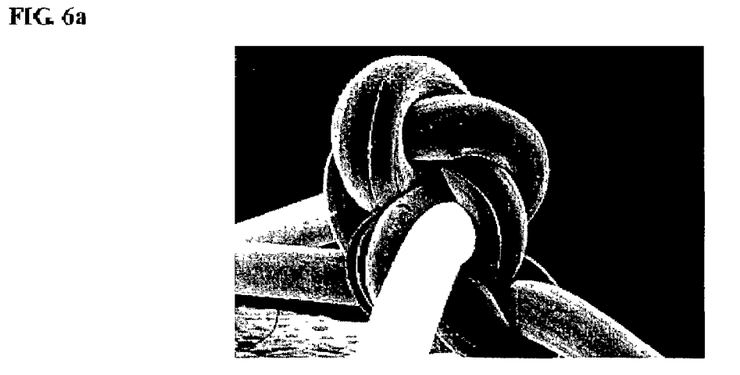
FIG. 6a represents the knot configuration of the suture obtained by co-extruding polydioxanone and polycaprolactone into the sea/island type.
Figure 6B:
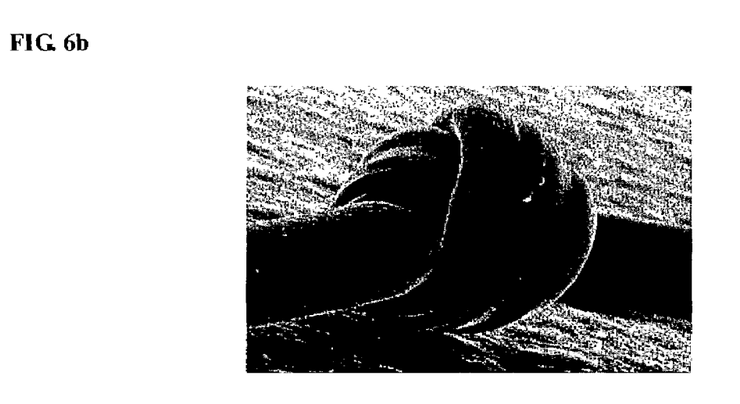
FIG. 6b represents the knot configuration of the suture obtained by co-extruding polylactide and polycaprolactone.
Figure 6C:
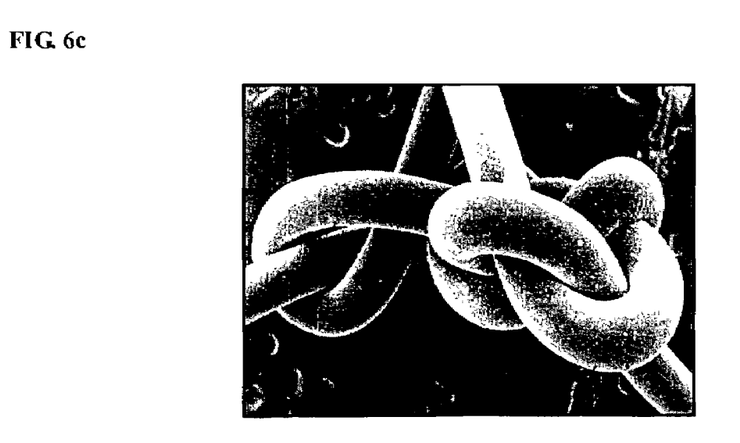
FIG. 6c is an SEM photograph showing the knot configuration of the suture prepared from polydioxanone only.

FIGS. 6a and 6b are SEM photographs comparing the characteristics of the knot obtained by the present invention with that of a conventional suture. FIG. 6a represents the knot configuration of the sea/island monofilament suture obtained from Example 1. FIG. 6b represents the knot configuration of the sea/island monofilament suture using polylactide and polycaprolactone obtained from Experimental Example 5. FIG. 6c represents the knot configuration of the monofilament suture prepared by using polydioxanone only. As shown in FIGS. 6a and 6b, the shape deformation of the suture obtained by the present invention occurs upon tying a knot, so that when the suture is firmly tied, there is little space left in the knot. On the contrary, the knot in the suture of FIG. 6c has much space therein, and thus, the tied knot is easily loosened.

EXPERIMENTAL EXAMPLE 4

Figure 7A:
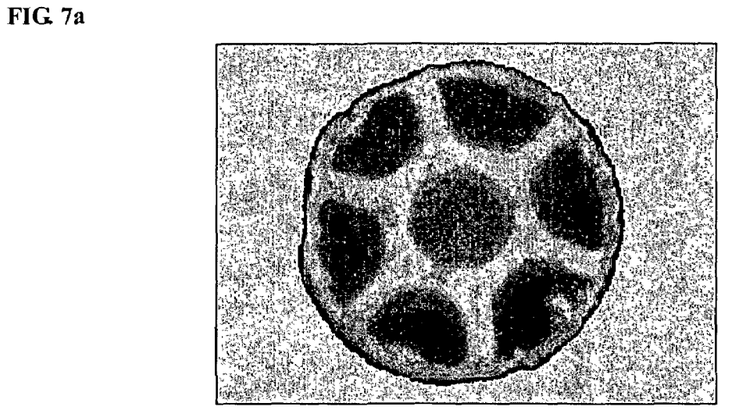
FIG. 7 illustrates DIC photographs showing that the cross section varies with the component ratios of the monofilament suture prepared in accordance with the present invention (by the content ratio of the sea component, 7a:70%, 7b:50%, 7c:20%).
Figure 7B:
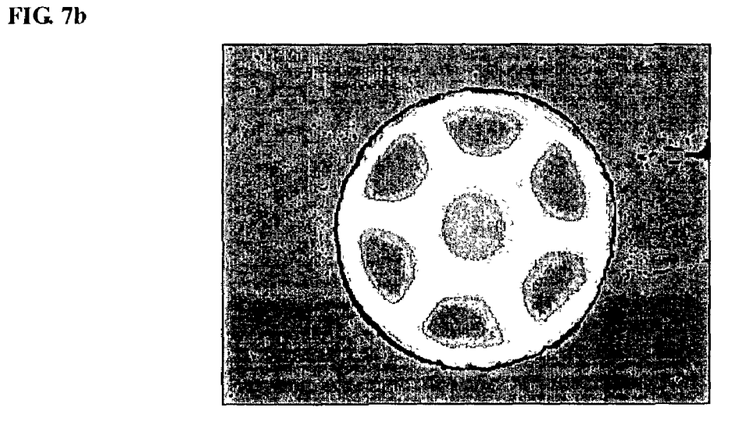

This example illustrates the relationship of the content ratio of the first polymer and the second polymer with the shape of a cross section of the suture. Procedures were carried out under the same conditions described in Example 2 except that the number of the island component was 7. After carrying out the experiment, the shapes of cross sections of the sutures are shown in FIG. 7. FIG. 7a represents the cross section of asuture having the first polymer in an amount of 70% by volume. FIG. 7b represents the cross section of the suture having the first polymer in an amount of 50% by volume and FIG. 7c represents the cross section of a suture having the first polymer in an amount of 20% by volume.

Figure 7C:
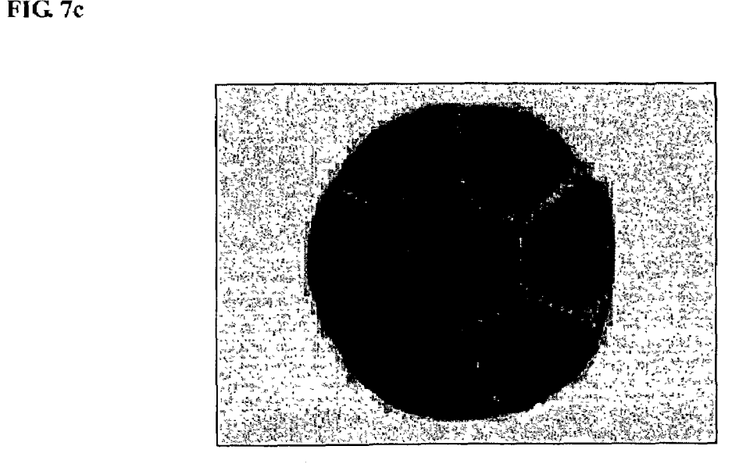

As shown in FIG. 7c, when the amount of the first polymer is 20% by volume, the area that the second polymer occupies becomes greater. Therefore, since the thickness of the first polymer surrounding with the second polymer is less, the drawability is likely to be less when preparing this suture. Even when the suture is prepared, its shape is likely to be changed by the annealing process, and thus, the surface of the suture is apt to become rough. Therefore, in order to prepare a suture suitable for the purpose of the present invention, preferably, the amount of the first polymer is 20% or more by volume, and more preferably, 50% or more by volume.

EXPERIMENTAL EXAMPLE 5

Polylactide, having a Young's modulus of 2.7 GPa and a melting point of 170~180° C., was used as the first polymer and polycaprolactone as the second polymer. A sea/island type monofilament suture was prepared by co-extruding the polymers in accordance with the parameters, terms and conditions as set forth in Table 12 below.

TABLE 12

| Conditions of Processing the Sea/Island Type Co-extruded Suture | | |
|---|---|---|
| Suture Size | EP 4 | |
| Polymer | Polycaprolactone | Polylactide |
| Young's modulus (GPa) | 0.7 | 2.7 |
| Melting Point (° C.) | 55~65 | 170~180 |
| Process Conditions | Extrusion Conditions | |
| Extruder | Ext. 1 (Island) | Ext. 2 (Sea) |
| Number of Island Component | 19 | — |
| Extruder screw, rpm | 8.3 | 2.2 |
| Manifold pressure (kgf/cm$^2$) | 80 | 80 |
| Temperature of Extruder (° C.) | | |
| Zone 1 | 185 | 190 |
| Zone 2 | 188 | 192 |
| Zone 3 | 200 | 195 |

TABLE 12-continued

| Conditions of Processing the Sea/Island Type Co-extruded Suture | | |
|---|---|---|
| Temperature of Manifold (° C.) | 200 | 195 |
| Temperature of Metering pump (° C.) | 200 | 195 |
| Temperature of Nozzle Pack Die (° C.) | 200 | |
| Capacity of Metering pump (cc/rev) | 1.2 | 1.2 |
| Revolution of Metering pump (rpm) | 6.3 | 2.7 |
| Temperature of Quenching bath (° C.) | 23 | |
| Winding Speed of Undrawn yarn (m/min) | 13.2 | |
| Drawing Conditions | | |
| First Roller (m/min) | 4 | |
| Temperature of First Drawing Oven (° C) | 120 | |
| Second Roller (m/min) | 17.7 | |
| Temperature of Second Drawing Oven (° C) | 120 | |
| Third Roller (m/min) | 18.6 | |
| Total Drawing Ratio | 4.7 | |

In order to compare physical properties, polydioxanone having a Young's modulus of 1.3 GPa as the first polymer and polycaprolactone as the second polymer were extruded under the same conditions as in Example 1, except that the winding speed and the drawing temperature were different.

Using the methods for measuring the physical properties explained above, diameter, knot strength, stiffness and knot slippage ratio of the prepared sutures were measured.

TABLE 13

| Comparison of physical properties of sutures | | | | |
|---|---|---|---|---|
| Composition | Diameter (mm) | Knot strength (Kgf) | Stiffness (mgf/mm$^2$) | Knot slippage ratio (%) |
| PDO/PCL | 0.481 | 4.22 | 75 | 0 |
| PLA/PCL | 0.409 | 1.12 | 98 | 0 |
| PLA | 0.458 | — | 245 | — |

As indicated in Table 13, both monofilament sutures prepared by co-extrusion in accordance with the present invention demonstrated excellent knot security with knot slippage ratios of 0%. In addition, the suture prepared by using polydioxanone as the first polymer is not stiff but is very flexible, and has excellent knot security. However, the suture prepared by using polylactide as the first polymer has low flexibility, which is caused by the high Young's modulus of polylactide. Therefore, to prepare monofilament sutures having excellent knot security and flexibility, it is preferable to use polymers that have a Young's Modulus of 2.0 GPa or less.

The above description will enable one skilled in the art to make a monofilament suture having improved knot security and flexibility. The sutures of the present invention are prepared by co-extruding a first absorbable polymer and a second absorbable polymer having a Young's modulus lower than the Young's modulus of the first polymer, wherein the first polymer surrounds the second polymer, said suture having improved knot security and flexibility. Although they are described to show the functionality of the monofilament suture of the present invention, these descriptions are not intended to be exhaustive. It will be immediately apparent to one skilled in the art that various modifications may be made without departing from the scope of the invention which is limited only by the following claims and their functional equivalents.

We claim:

1. A monofilament suture, having improved knot security and flexibility, comprising a first absorbable polymer and a second absorbable polymer having a Young's modulus lower than the Young's modulus of the first polymer said first polymer is co-extruded with said second polymer forming a sea/island type suture comprising a plurality of islands wherein the first polymer is the sea component and the second polymer is the island component, and wherein the Young's modulus of the first polymer and the second polymer is 3.0 GPa or less, and wherein the difference of the Young's modulus between the first polymer and the second polymer is 0.3 GPa or more.

2. The monofilament suture of claim 1, wherein the amount of the first polymer is 10 to 90% by volume and the amount of the second polymer is 10 to 90% by volume.

3. The monofilament suture of claim 1, wherein the amount of the first polymer is 50 to 90% by volume and the amount of the second polymer is 10 to 50% by volume.

4. The monofilament suture of claim 1, wherein the first polymer and the second polymer are homopolymers or are copolymers synthesized from monomers selected from the group consisting of glycolide, glycolic acid, lactide, lactic acid, caprolactone, dioxanone, trimethylene carbonate and ethyleneglycol.

5. The monofilament suture of claim 4, wherein the first polymer is a homopolymer or is a copolymer synthesized from monomers selected from the group consisting of glycolide, glycolic acid, dioxanone and lactide.

6. The monofilament suture of claim 4, wherein the second polymer is a homopolymer or is a copolymer synthesized from monomers selected from the group consisting of caprolactone, trimethylene carbonate, DL-lactide and ethylene glycol.

7. The monofilament suture of claim 1, wherein the melting point of the first polymer is higher than the melting point of the second polymer.

8. The monofilament suture of claim 1, wherein the Young's modulus of the first polymer is 2.0 GPa or less and the Young's modulus of the second polymer is 1.5 GPa or less.

9. The monofilament suture of claim 8, wherein the Young's modulus of the first polymer is 1.0~1.5 Gpa and the Young's modulus of the second polymer is 1.2 GPa or less.

10. The monofilament suture of claim 9, wherein the Young's modulus of the second polymer is 0.4~1.2 GPa.

* * * * *